Figure 1:
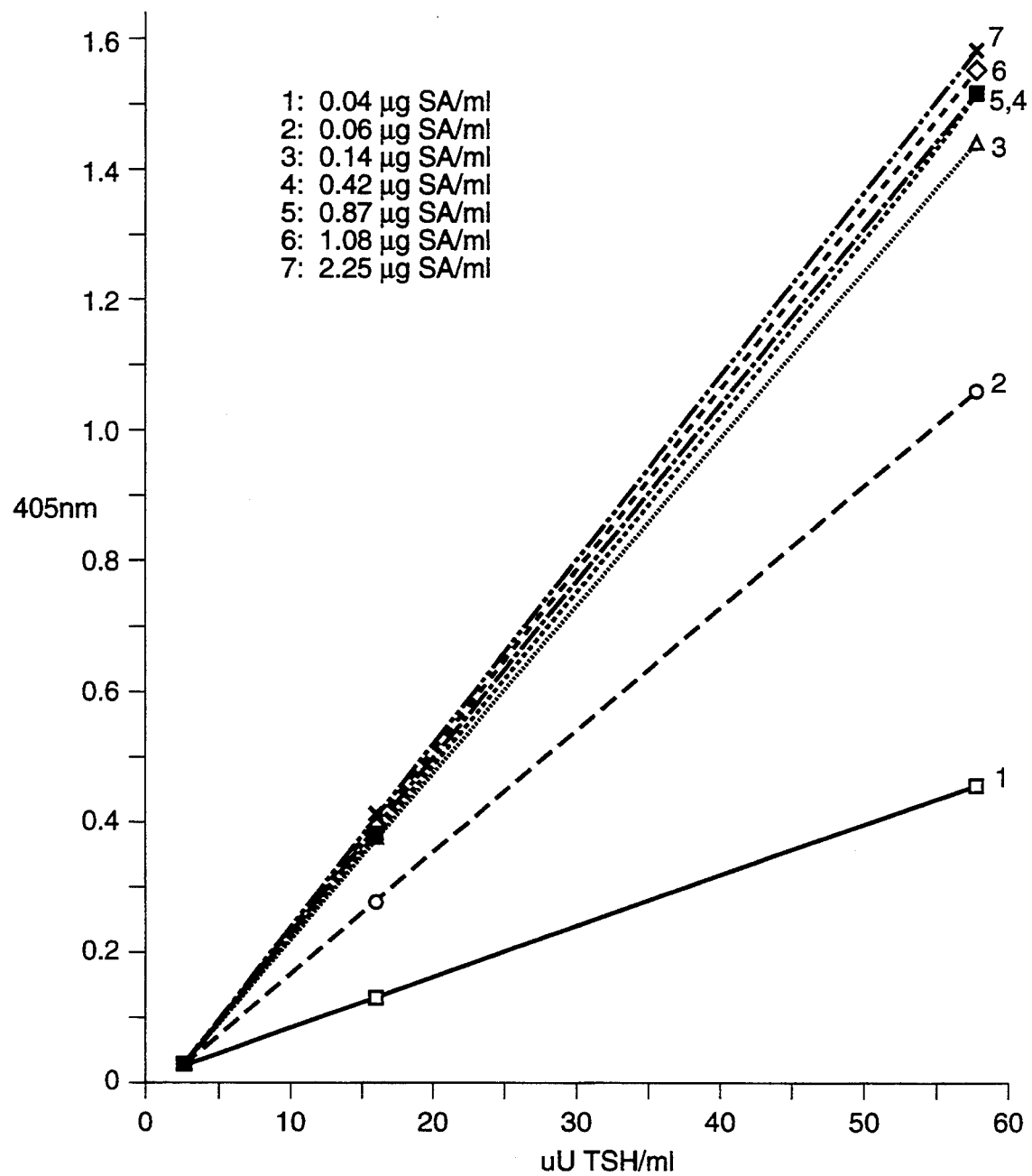

United States Patent [19]
Schmitt et al.

[11] Patent Number: 5,362,624
[45] Date of Patent: Nov. 8, 1994

[54] PROCESS FOR THE DETERMINATION OF AN IMMUNOLOGICALLY DETECTABLE SUBSTANCE AND A SUITABLE REACTION VESSEL THEREFOR

[75] Inventors: Urban Schmitt, Oberhausen; Eberhard Maurer, Weilheim; Wolfgang Rüdinger, Birkenau; Rolf Deeg, Bernried; Thomas Geiger, Diessen; Wolf D. Engel, Feldafing, all of Germany

[73] Assignee: Boehringer Mannheim GmbH, Mannheim, Germany

[21] Appl. No.: 925,300

[22] Filed: Aug. 5, 1992

Related U.S. Application Data

[63] Continuation of Ser. No. 691,685, Apr. 25, 1991, abandoned, which is a continuation of Ser. No. 356,336, May 24, 1989, abandoned.

[30] Foreign Application Priority Data

May 25, 1988 [DE] Germany .............................. 3817716
Jan. 20, 1989 [DE] Germany .............................. 3901638

[51] Int. Cl.$^5$ ................... C01N 33/576; C01N 33/547
[52] U.S. Cl. ..................................... 435/7.5; 435/820; 436/500; 436/532; 436/811
[58] Field of Search ............... 436/501, 518, 527, 500, 436/532, 811; 435/7.5, 820

[56] References Cited

U.S. PATENT DOCUMENTS

| | | | |
|---|---|---|---|
| Re. 34,312 | 7/1993 | Geiger et al. | 435/5 |
| 4,945,042 | 7/1990 | Geiger et al. | 436/538 |
| 5,061,640 | 10/1991 | Lischer et al. | 436/527 |

FOREIGN PATENT DOCUMENTS

| | | | |
|---|---|---|---|
| 2601455 | 7/1986 | France . | |
| 3640412 | 6/1988 | Germany . | |
| 71359 | 4/1986 | Japan | 436/501 |
| 2181840 | 4/1987 | United Kingdom . | |

*Primary Examiner*—Mary E. Ceperley
*Attorney, Agent, or Firm*—Felfe & Lynch

[57] ABSTRACT

For the determination of an immunologically detectable substance based on a heterogeneous immunoassay by use of a solid phase on which one of the immunologically active reaction components is bound, a reaction vessel is used as the solid phase on the inner surface of which streptavidin or avidin is bound in such an amount that 0.1 to 2.5 μg are present per ml reaction volume.

A suitable reaction vessel for this has optically transparent wall areas which face one another and has avidin or streptavidin coated walls which are at least partially within the inner wall region intended as a receptacle for liquid, wherein the inner space of the container intended as a receptacle for liquid and the respective streptavidin or avidin content of the coating are so matched that 0.1 to 2.5 μg streptavidin or avidin are present per ml reaction volume.

2 Claims, 5 Drawing Sheets

PROCESS FOR THE DETERMINATION OF AN IMMUNOLOGICALLY DETECTABLE SUBSTANCE AND A SUITABLE REACTION VESSEL THEREFOR

This application is a continuation of application Ser. No. 691,695, filed Apr. 25, 1991, now abandoned, which is a continuation of Ser. No. 356,336, filed May 24, 1989, now abandoned.

The invention concerns a process for the determination of an immunologically detectable substance based on a heterogeneous immunoassay by use of a solid phase on which one of the immunologically active reaction components is bound, a suitable reaction vessel therefor as well as use of a standard reaction vessel.

Immunoassay procedures are often used to determine substances which can be specifically bound. In this process one partner of a binding pair capable of specific binding to one another is reacted with its specific receptor which is labelled in a known way. The conjugate of both these substances can then still react with a receptor which is specific for the conjugate or for one of the two parts of the conjugate. There are many variants of these immunological procedures. In such methods it is advantageous if one of the receptors is present bound to a solid phase. This facilitates the separation of the bound and non-bound reaction partners. For the determination of the substance capable of being specifically bound, the amount of labelled reaction partner bound to the solid phase or of labelled reaction partner present in the solution is measured and related to the amount of the reaction partner to be determined according to known procedures.

Plastic tubes or microtitre plates on the inner surface of which the reaction partner is bound, or spheres on the outer surface of which the reaction partner is bound, are usually used as the solid phase for immunological methods.

In these methods the binding of the specific reaction partner to the respective surface must be carried out in such a way that it does not lose its ability to specifically bind to the substance which is capable of specific binding to it. For this reason the reaction partner is usually bound adsorptively to the solid phase. It was therefore already suggested that the binding of the reaction partner to the solid phase should be achieved via a coupling agent which mediates the binding. In this process one should take care that the binding of the reaction partner to the binding agent does not destroy the region of the molecule which specifically reacts or alternatively that the reaction partner is bound in such a way that its reactive site is facing away from the solid phase and towards its binding partner.

A disadvantage of all these known processes is that a special solid phase has to be provided for each specific reaction. This means that for each individual test another solid phase has to be produced, stored and then used for the determination, which is tedious.

It is therefore the object of the present invention to provide a process and a reaction vessel which are suitable for many different methods of detection. For routine clinical diagnosis many different parameters such as hormones, tumour markers, as well as parameters for infection, allergy or fertility are determined from a single blood sample. The concentration of the parameters to be determined covers a wide range. Parameters in low concentrations such as for example TSH and prolactin are in the range of $10^{-10}$ to $10^{-12}$ mol/l, whereas parameters in high concentrations like $T_3$ and $T_4$ are at a concentration of about $10^{-7}$ to $10^{-8}$ mol/l. For this purpose it would be desirable if a different tube did not have to be used in every case for the individual determinations, but rather if a standard reaction vessel could be used for all determinations.

This object was achieved by a process for the determination of an immunologically detectable substance based on a heterogeneous immunoassay by use of a solid phase on which one of the immunologically active reaction components is bound, wherein a reaction vessel is used as the solid phase on the inner surface of which streptavidin or avidin is bound in such an amount that 0.1 to 2.5 $\mu$g are present per ml reaction volume. The amount quoted refers to streptavidin or avidin which is accessible to the binding partner in the form of a biotinylated protein or hapten during the course of the immunological reaction.

The process according to the present invention is applicable to all methods of determination in which the receptor, which can be an antibody or an antigen, which is to be immobilized on the solid phase is conjugated with biotin. The streptavidin or avidin respectively, bound to the solid phase according to the present invention, adhere well to all tube materials and the binding is stable against detergents. In the process of establishing calibration curves which are necessary for the evaluation of many immunological methods, the streptavidin or avidin bound to the solid phase yield steep calibration curves with small blank readings which lead to an increase in the accuracy. A further advantage is that lot to lot variations in the amount of coated streptavidin had only negligible influences on the results of measurements. The particular advantage of the process according to the present invention is that the amount of streptavidin or avidin bound can be so adjusted that the solid phase can be used for all known processes based on heterogeneous immunoassays. A further advantage is that several substances, especially antibodies, but also antigens, can be determined simultaneously with the process according to the present invention. This will be elucidated in more detail in Example 7.

In a particularly preferred embodiment the reaction vessel used as the solid phase is at the same time used as a cuvette for the photometric determination of the label. This is particularly advantageous since only a single vessel is necessary to carry out the entire reaction. In this case the reaction vessel is so constructed that it has two optically transparent wall areas facing one another. The entire wall area can be coated with streptavidin or avidin.

According to the present invention a reaction vessel is used as the solid phase on the inner surface of which streptavidin or avidin is bound. The binding of streptavidin or avidin is carried out by methods known to the expert (EP-A 0 122 209). The streptavidin or avidin can either be bound directly to the solid phase or alternatively bound via a spacer or substances which mediate the binding.

In a preferred embodiment of the present invention streptavidin or avidin is coupled to a soluble protein with a molecular weight above about 500,000 and then this conjugate is adsorbed to a hydrophobic solid phase as described for example in the patent application DE-A36 40 412. It is preferable to use a protein which has been made hydrophobic.

This increase in hydrophobicity can result from the application of heat, treatment with acid, denaturing agents and/or chaotropic ions and/or by chemical coupling to a hydrophobic compound. Treatment with these agents also leads to an increase in the molecular weight. The increase in molecular weight can be also achieved by cross-linking with a bi-or polyfunctional protein reagent.

Acetic acid, propionic acid, lactic acid or hydrochloric acid can for example be used as the acid. The usual concentrations are 1 to 100 mmol/l with reaction times from 10 min to 16 hours.

Suitable chaotropic ions are for example thiocyanates, iodides, fluorides, bromides, perchlorates and sulphates. Suitable denaturing agents are for example guanidine hydrochloride or urea. The concentrations of these are usually from 10 mmol/l to 6 mol/l.

For the derivatisation with hydrophobic compounds soluble fatty acids, lipoids in a low or high molecular weight form as well as synthetic polymers such as polypropylene glycol or soluble copolymers of polystyrene are preferably used. The derivatisation is carried out by methods familiar to the expert.

The cross-linking by means of bi- or polyfunctional compounds is carried out with known protein binding reagents. These are compounds which have at least two functional groups which can be either the same or different and which can react with functional groups of proteins by means of these functional groups. It is preferred to use compounds which consist of an alkyl chain at the end of which succinimide, maleimide, and/or aldehyde groups are located.

The protein is cross-linked with the bi- or polyfunctional compound in a known way by reacting the soluble protein and the bi- or polyfunctional compound.

In order to increase the hydrophobicity and/or to cross-link, it is preferable to use proteins with a molecular weight from 10,000 to 700,000 daltons. Particularly preferred is bovine serum albumin, lipase or immunoglobulin.

Streptavidin or avidin is then coupled to the protein using a known method. Suitable coupling methods are described for example in Ishikawa, J., Immunoassay 4 (1983), 209–327.

The conjugate obtained from streptavidin or avidin and protein is then adsorbed on to the plastic surface which serves as the solid phase. Before the conjugate of protein and streptavidin or avidin is adsorbed onto the hydrophobic solid phase it is also possible to chemically or physically pretreat the solid phase. Thus for example a plastic surface can be swollen in advance or activated in another known manner. The adsorptive binding to the solid phase results from strong and weak interactions, hydrophobic forces, dipole-dipole or ion-dipole interactions.

Reaction vessels made of supporting materials with a surface tension which is smaller than the surface tension of the soluble hydrophobic protein i.e. which are more hydrophobic than protein are particularly suitable as the hydrophobic solid phase. Use of supporting materials with a surface tension of 40 erg/cm$^2$ is preferred. Particularly suitable are polystyrene, polymethacrylate, teflon, polyamide, copolymers of styrene and acrylonitrile, glass and cellulose products.

The solid phase material produced according to the present invention is used in the determination of many different parameters. In this process one of the substances capable of binding to the parameter to be determined is conjugated with biotin which in turn binds to the streptavidin or avidin respectively bound to the solid phase. By this means the specific complexes which form as a result of the immunoassay process can be immobilized and then determined. Therefore in accordance with the present invention as much streptavidin or avidin respectively is bound to the solid phase that per ml reaction volume 0.1 to 2.5 $\mu$g are available for binding to the biotinylated substance capable of specific binding.

The said reaction volume denotes the sum of sample volume and test reagent volume.

It is preferred to coat the solid phase material such that 1 to 2 $\mu$g streptavidin or avidin respectively are available for binding to the biotinylated substance capable of specific binding. The amounts of the biotinylated substance capable of specific binding is in the range of from $10^{-16}$ to $10^{-8}$ mol/reaction volume.

A further embodiment of the present invention is a reaction vessel with optically transparent wall areas which face one another and with avidin or streptavidin coated walls which are at least partially within the inner wall region intended as a receptacle for liquid, wherein the inner space of the container intended as a receptacle for liquid and the respective streptavidin or avidin content of the coating are so matched that 0.1 to 2.5 $\mu$g streptavidin or avidin are present per ml reaction volume.

This reaction vessel is particularly suitable for carrying out the process according to the present invention. Since it has optically transparent wall areas which face one another and also a coating of streptavidin or avidin it can be used simultaneously to carry out the reaction and for the photometric determination. As a result of the coating with 0.1 to 2.5 $\mu$g streptavidin or avidin respectively per ml reaction volume, this reaction vessel can be used for the determination of different parameters on the basis of a heterogeneous immunoassay.

The reaction vessel constitutes the solid phase. It consists of materials which are usually used for this purpose such as plastics, glass etc. The optically transparent wall areas also consist of known materials. Particularly preferred in this case are polystyrene, copolymers of polystyrene, polycarbonates, polyacrylates and polymethacrylates.

Streptavidin or avidin can either be coated directly or via a carrier material or a spacer. For example the binding of streptavidin or avidin to a soluble protein with a molecular weight above 500,000 daltons which is then adsorbed to the inner surface of the reaction vessel is suitable.

An embodiment of the invention is also the use of a standard reaction vessel for the determination of different parameters using processes based on immunoassays, which consists of a vessel on the inner surface of which streptavidin or avidin is bound in such an amount that for the test reaction 0.1 to 2.5 $\mu$g streptavidin or avidin are available per ml reaction volume.

According to the present invention a process and a reaction vessel are provided in which streptavidin or avidin are bound permanently and with good adhesion to the inner surface of a reaction vessel which serves as a solid phase. The adhesion is so good that even the addition of detergents does not lead to the detachment of the substance. The reaction vessel provided according to the present invention can be universally employed and is suitable for carrying out methods of determination for very many parameters and therefore facilitates the performance of routine determinations.

Figure 2:
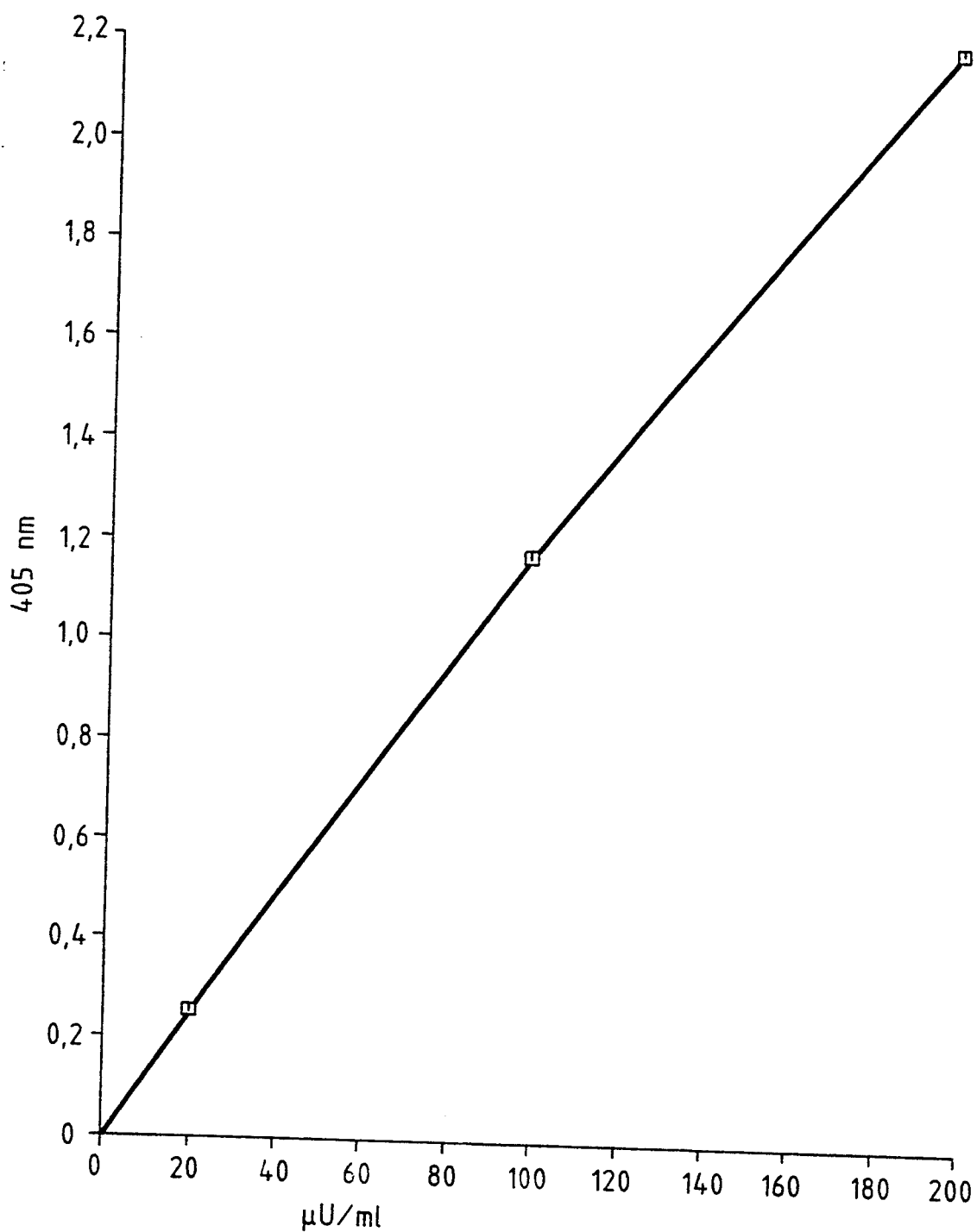
Figure 3:
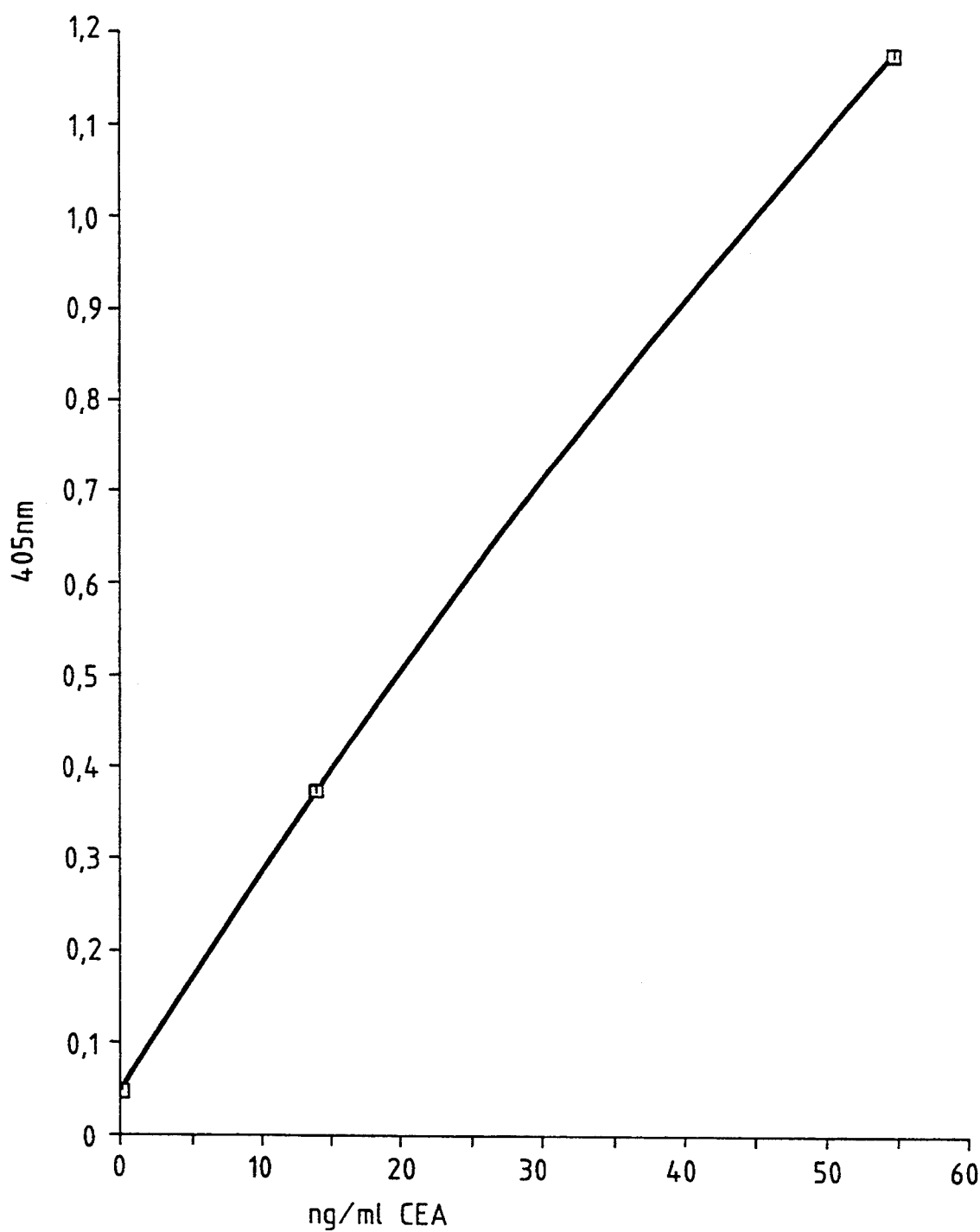

The invention is elucidated by the following figures and examples. The figures show:

FIG. 1 a family of calibration curves for a TSH determination using immobilized streptavidin in various amounts and biotinylated anti-TSH-antibody;

FIG. 2 a calibration curve for a prolactin test;

FIG. 3 a calibration curve for a CEA-test and

Figure 4:
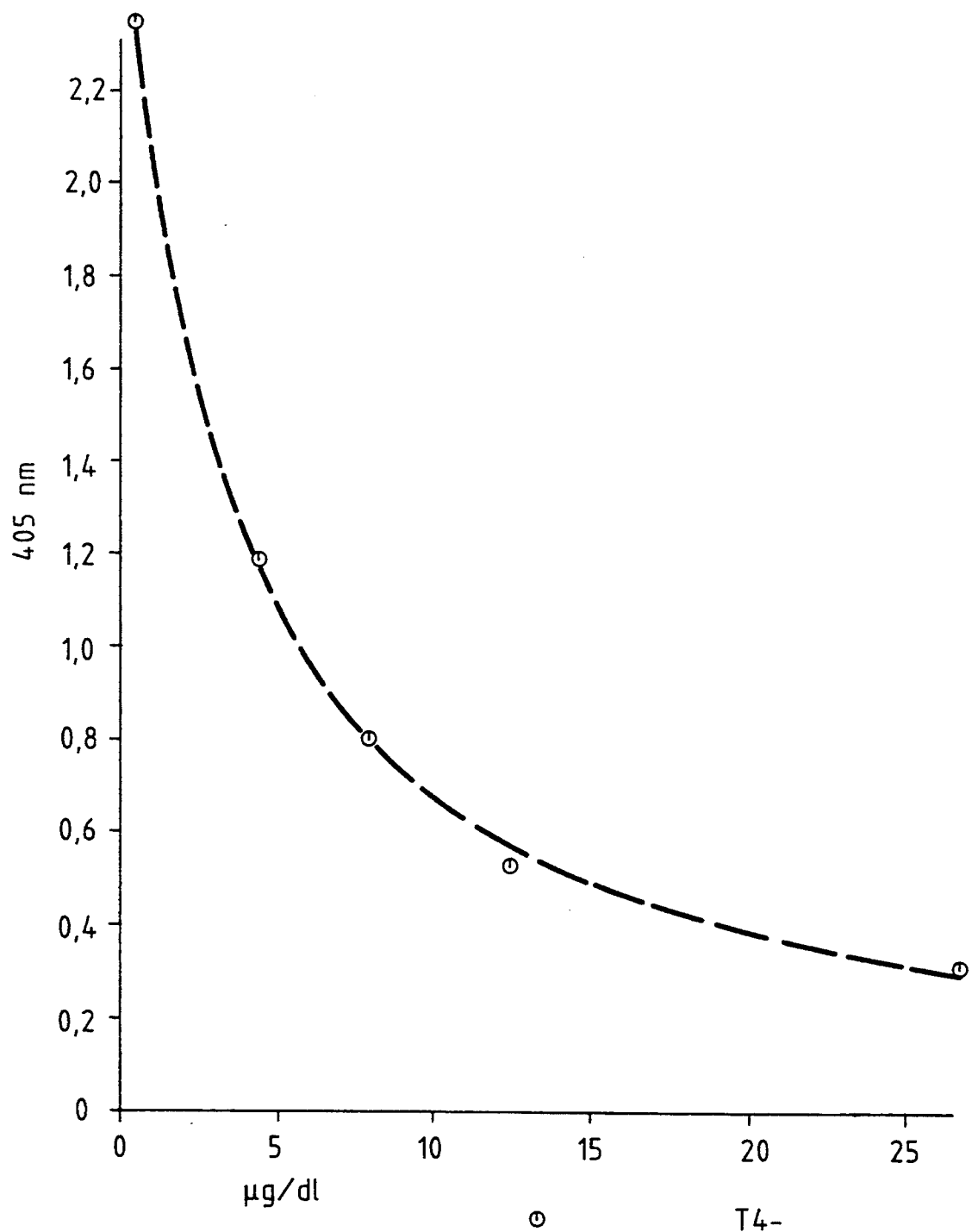

FIG. 4 a calibration curve for a T4-test.

Figure 5:
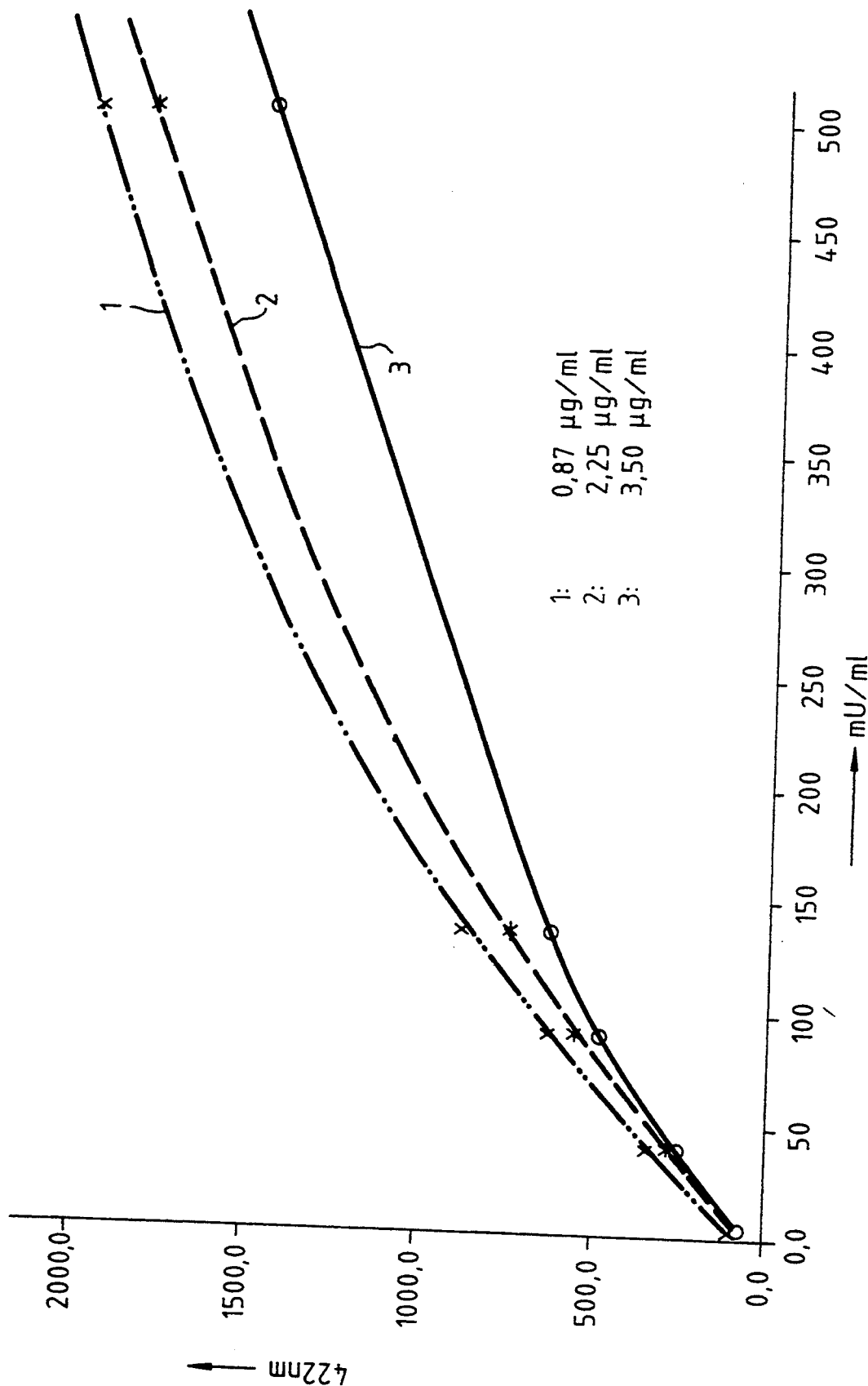

FIG. 5 a family of calibration curves for an anti-HBs determination using immobilized streptavidin in different amounts.

The monoclonal antibodies against TSH used in the examples originate from hybridoma cell lines which were deposited at the European Collection of Animal Cell Cultures, Porton Down, GB, under the numbers ECACC 87122201 and ECACC 87122202.

EXAMPLE 1

The binding to the solid phase of the conjugate according to the present invention and of the hydrophobic protein and streptavidin was investigated:

Thermally aggregated BSA, from now on referred to as thermo-BSA, was prepared as follows: 1 g BSA was dissolved in 100 ml of 50 mmol/l potassium phosphate solution with a pH of 7.0, and was heated to 70° C. and kept at this temperature for 4 hours during which it was gently stirred. The solution was cooled down, filtered and adjusted to a concentration of 50 mg/ml. Afterwards it was dialyzed against a thirtyfold volume of redistilled water.

Preparation of a conjugate of streptavidin with thermo-BSA: streptavidin was isolated from Streptomyces avidinii and was converted by maleimido-hexanoyl-N-hydroxy-succinimide to a streptavidin containing maleimido groups. Thermo-BSA was converted with s-acetyl-mercapto-succinic acid anhydride and the protected SH-groups were afterwards released by the addition of hydroxylamine. The desired conjugate was then obtained by mixing the streptavidin containing maleimido groups and the thermo-BSA containing SH-groups.

Plastic tubes made of polystyrene were then coated with the streptavidin-thermo-BSA-conjugate. The coating of the tubes was carried out with 1.5 ml of a streptavidin-thermo-BSA-solution for 18 to 24 hours, whereby the molar ratio of both components was 1.8:1 (10μg/ml) in 40 mmol/l sodium phosphate buffer, pH 7.4 at 20° C.

After aspiration of the tubes they were recoated with 1.8 ml of a solution containing 2% sucrose, 0.9% sodium chloride and 0.3% BSA for 30 min at 20° C. After drying (24 hours at 20° C. and 40% relative humidity) the tubes were ready for use and stable.

EXAMPLE 2

One-step test for TSH

Biotinylated monoclonal anti-TSH-antibody was prepared. For this purpose the anti-TSH-antibody, ECACC 87122201, was converted with biotin in the usual way, whereby the coupling took place via amino groups. Antibody and biotin were used in the proportion of 1:16. 400 ng of the biotinylated antibody thus obtained were dissolved in 1 ml buffer (40 mmol/l sodium phosphate, 0.5% Pluronic F68, 0.2 mol/l sodium tartrate as well as 0.01% phenol) and then incubated for two hours in a coated tube as described in Example 1 with 200 μl sample or standard solution respectively containing a known amount of TSH and 75 mU of an anti-TSH-antibody conjugated with peroxidase (ECACC 87122202). Afterwards it was washed three times with tap water and 1 ml ABTS-substrate solution was added. After one hour the absorption was measured at 405 nm. The results are shown in FIG. 1. It turns out that a satisfactory result is obtained with immobilized streptavidin when an amount of more than 0.1 μg/ml test volume is used.

The streptavidin required for binding of the biotinylated antibody used in the test was determined. For this the amount of freely available biotin was determined according to the method of Bayer, Edward A., Meir-Wilchek, Analytical Biochemistry 154 (1986), 367–370. Assuming that 1 μg antibody was biotinylated in an antibody to biotin ratio of 1:15 (Guesdon, I. L., J. Histochem. Cytochem. 27 (1979) 1131–1139), it follows that 1 to 2 mol biotin per mol antibody are available for binding, i.e. 1.5 to 3 ng biotin are freely accessible per μg antibody.

A tube coated with 10 μg/ml streptavidin-thermo-BSA-conjugate (Example 1) has a binding capacity for biotin of 15 to 20 ng per ml test volume, determined with radioactive $^{14}C$-biotin.

The binding capacity of the streptavidin tubes for biotinylated immuno-γ-globulin is 1.7 to 2 μg/ml test volume. The determination was carried out with $^{125}I$-labelled γ-globulin (labelled according to the method of McConahey and Dixon 1966, Int. Arch. Allergy 29/185).

EXAMPLE 3

Prolactin test

Prolactin is determined by a one-step-sandwich-immunoassay. A reagent of the following composition is used for the detection:

50 mU/ml of a conjugate of POD and a monoclonal antibody specific for prolactin, 40 mmol/l phosphate buffer, pH 7.0

0.5% Pluronic F65 (polyoxyethylene polypropylene)

0.2 mol/l sodium tartrate 0.01% phenol 0.2% bovine serum albumin 400 ng/ml of a biotinylated monoclonal antibody against prolactin.

Both monoclonal antibodies are only required to detect prolactin and to be directed against the various epitopes of prolactin. 1 ml of this reagent and 50 μl sample were incubated for 30 min at room temperature in a polystyrene tube coated with streptavidin-thermo-BSA-conjugate, obtained according to Example 1. Afterwards it was washed three times with tap water. 1 ml ABT®-substrate solution was added for the test reaction. The absorbance was measured photometrically after 30 min at 405 nm. The results are shown in FIG. 2.

ABT®: 2.2'-azino-di-[3-ethylbenzthiazoline-6-sulphonate]-di-ammonium salt

EXAMPLE 4

CEA test

CEA was determined in a sample solution by a one-step-sandwich-immunoassay. The reagent used contained the following:

120 mU/ml of a conjugate of POD and a monoclonal antibody against CEA, 40 mmol/l phosphate buffer, pH 7.0
0.5% Pluronic F68
0.2 mol/l sodium tartrate
0.01% phenol
0.2% bovine serum albumin
500 ng/ml of a biotinylated monoclonal antibody against CEA.

The only requirements for both monoclonal antibodies against CEA are that they detect CEA and that each is directed against a different epitope of CEA.

1 ml reagent and 100 μl sample were incubated for 2 hours at room temperature in a polystyrene tube coated with streptavidin-thermo-BSA, obtained according to Example 1. Afterwards it was washed three times with tap water. 1 ml ABT®-substrate solution was added for the test reaction. After one hour the absorbance was measured photometrically at 405 nm. The results are shown in FIG. 3.

EXAMPLE 5

T4 test

T4 was determined in a competitive immunoassay using biotinylated anti-T4-antibodies. For this purpose 500 μl of a reagent consisting of:
100 mU/ml thyroxine-POD-conjugate (prepared according to EP 209 155)
120 mmol/l barbiturate
18.2 mmol/l phosphate buffer, pH 8.6
0.04% by weight ANS (8-anilino-1-naphthaline-sulphonic acid)
0.2 % by weight bovine serum albumin,
as well as 20 μl sample were incubated for 10 min at room temperature in a polystyrene tube coated with streptavidin-thermo-BSA-conjugate, obtained according to Example 1. Afterwards 500 μl of a second reagent consisting of:
1 μg/ml biotinylated polyclonal antibody against T4,
120 mmol/l phosphate buffer, pH 8.6,
0.04% by weight ANS (8-anilino-1-naphthaline-sulphonic acid),
0.2% by weight bovine serum albumin,
were added and incubated for a further 30 min at room temperature. After washing it three times with tap water 1 ml ABT®-substrate solution was then added and incubated for 30 min at room temperature. Afterwards the absorbance was measured photometrically at 405 nm. The results are shown in FIG. 4.

EXAMPLE 6

Anti-HB$_s$ test

HB$_s$-antibodies were determined in a one-step-sandwich-immunoassay. A reagent with the following composition was used for the determination:
60 mU/ml of a conjugate of POD and HB$_s$-antigen
40 mmol/l phosphate buffer, pH 7.0
200 mmol/l sodium tartrate
0.5% by weight Pluronic F68
0.01% by weight phenol
0.2% bovine serum albumin
0.1% by weight bovine-IgG
150 ng/ml biotinylated HB$_{sAg}$ (prepared according to Immunol. Letters 8 (1984), 273).

1 ml of this reagent and 200 μl sample were incubated for 4 hours at room temperature in a polystyrene tube coated with a conjugate of streptavidin-thermo-BSA. After washing it three times with tap water 1 ml of ABTS-substrate solution was added for the test reaction. After 60 min the absorbance at 422 nm was measured photometrically.

The anti-HB$_s$-test was performed in tubes using different amounts of immobilized streptavidin. The results are shown in FIG. 5. It can be seen that when streptavidin is used in amounts which are more than those recommended in the present invention then the test becomes significantly less sensitive.

EXAMPLE 7

Anti-HIV test

HIV-antibodies are determined in a two-step-sandwich-immunoassay. A reagent with the following composition was used for the determination.
Reagent 1
$10^{-7}$ mol/l each of one or several biotinylated HIV-antigens
40 mmol/l phosphate buffer, pH 7.0
0.9 % by weight sodium chloride
10% by volume bovine serum The following were used as antigens: HIV1-antigen produced by genetic engineering corresponding to HIV1-gp41 (gp41-rek., Centocor TM -p121) and HIV1-p24 (p24-rek., Centocor TM -pg2), chemically synthesized peptide from HIV1-gp41 (gp41-pep, Wang et al., PNAS, 83, 6159, 1986) and HIV2-gp32 (gp32-pep, Gnann, J. W. et al., Science, 237, 1346, 1987). These antigens were labelled with biotin as described by Leary et al., PNAS, 80, 4045 (1983).
Reagent 2
20 mU/ml of a conjugate of sheep antibodies against human immunoglobulin and POD
40 mmol/l phosphate buffer, pH 7.0
0.05% by weight Tween 20
0.2% bovine serum albumin
0.2% bovine-IgG 1 ml of reagent 1 and 10 μl human serum or plasma were incubated for 1 hour at room temperature in a polystyrene tube coated with a conjugate of streptavidin-thermo-BSA. Afterwards the tube was washed three times with tap water and incubated for 1 hour at room temperature with 1 ml reagent 2. The tube was again washed three times with tap water and 1 ml ABTS substrate solution was added for the test reaction. After 60 min the absorbance at 422 nm was measured photometrically.

The anti-HIV-test was carried out using individual HIV-antigens and combinations of antigens. As a result it was demonstrated that the test procedure in polystyrene tubes coated with a conjugate of streptavidin-thermo-BSA is suitable for the determination of individual antigen-specific antibodies as well as for the simultaneous determination of several antibodies or antibody populations (screening test; table 1), irrespective of whether these antibodies are directed against the same virus or against several viruses or against the antigens of interest.

TABLE 1

| | Human serum sample | | | | | |
|---|---|---|---|---|---|---|
| HIV-Antigens | Neg. | Anti-HIV I | Anti-HIV I | Anti-HIV I | Anti-HIV II | Anti-HIV I | Anti-HIV II |
| Amount of HIV-Antigen | | | | | | | |
| gp41-rek. | 52 | 1250 | 812 | 521 | 102 | 223 | 75 |
| p24-rek. | 43 | 786 | 1515 | 212 | 491 | 1531 | 263 |
| gp41-pep | 71 | 831 | 301 | 295 | 63 | 52 | 59 |

TABLE 1-continued

| HIV-Antigens | Human serum sample | | | | | |
|---|---|---|---|---|---|---|
| | Neg. | Anti-HIV I | Anti-HIV I | Anti-HIV I | Anti-HIV II | Anti-HIV I | Anti-HIV II |
| gp32-pep | 38 | 41 | 50 | 62 | 1819 | 45 | 810 |
| gp41-,p24-rek. | 45 | 1402 | 1818 | 618 | 550 | 1559 | 266 |
| gp41-,p24-rek. + gp32-pep | 55 | 1380 | 1753 | 599 | 1723 | 1529 | 878 |

We claim:

1. Method for determining presence of antibodies to hepatitis B surface antigen in a sample comprising contacting a reaction vessel having a fixed reaction volume, an outer surface and an inner surface, wherein said inner surface is coated with a complex comprising avidin or streptavidin, wherein said avidin or streptavidin is present in an amount ranging from 0.1 to 2.5 ug per ml of reaction volume of said reaction vessel, with biotinylated, hepatitis B surface antigen to bind it thereto, contacting bound biotinylated hepatitis B surface antigen with said sample to bind antibodies to hepatitis B surface antigen to said bound, biotinylated hepatitis B surface antigen, contacting said bound antibodies with labeled hepatitis B surface antigen, and determining binding of said labeled hepatitis B surface antigen as a determination of antibodies to hepatitis B surface antigen in said sample.

2. Method for determining presence of thyroid stimulating hormone (TSH) in a sample, comprising contacting a reaction vessel having a fixed reaction volume, an outer surface and an inner surface, wherein said inner surface is coated with a complex comprising avidin or streptavidin, wherein said avidin or streptavidin is present in an amount ranging from 0.1 to 2.5 ug per ml of reaction volume of said reaction vessel, with biotinylated antibodies specific to TSH to bind said biotinylated antibodies to said reaction vessel, contacting bound biotinylated antibodies with said sample to bind TSH to said biotinylated antibodies, contacting bound TSH with a labeled antibody which binds to bound TSH, and determining bound labeled antibody as a determination of TSH in said sample.

* * * * *